(12) United States Patent
Brown

(10) Patent No.: US 6,495,610 B1
(45) Date of Patent: Dec. 17, 2002

(54) METHANOL AND HYDROCARBONS

(75) Inventor: Frank Clifford Brown, London (GB)

(73) Assignee: Imperial Chemical Industries PLC, London (GB)

( * ) Notice: Subject to any disclaimer, the term of this patent is extended or adjusted under 35 U.S.C. 154(b) by 0 days.

(21) Appl. No.: 09/597,067

(22) Filed: Jun. 19, 2000

(51) Int. Cl.$^7$ ............................................. C07C 27/00
(52) U.S. Cl. ...................... 518/706; 518/700; 518/702; 518/704
(58) Field of Search ................................ 518/700, 702, 518/704, 706

(56) References Cited

U.S. PATENT DOCUMENTS 6,248,794 B1 * 6/2001 Gieskes ...................... 518/700

FOREIGN PATENT DOCUMENTS

WO          99/03807      *   1/1999

* cited by examiner

Primary Examiner—Jafar Parsa
(74) Attorney, Agent, or Firm—Pillsbury Winthrop LLP

(57) ABSTRACT

Methanol and higher hydrocarbons are produced by synthesising the hydrocarbons from a synthesis gas containing hydrogen, carbon monoxide and carbon dioxide by the Fischer-Tropsch reaction, separating the higher hydrocarbons, and synthesising methanol from the residual gas. Preferably hydrogen is separated from the synthesis gas prior to the Fischer-Tropsch reaction and at least part of the separated hydrogen is added to the residual gas prior to methanol synthesis.

8 Claims, 1 Drawing Sheet

METHANOL AND HYDROCARBONS

This invention relates to the production of methanol and higher hydrocarbons, i.e. hydrocarbons containing four or more carbon atoms. Higher hydrocarbons may be made from a synthesis gas containing hydrogen and carbon monoxide by the known art of the Fischer-Tropsch process. Likewise methanol is often produced from a synthesis gas containing hydrogen and carbon oxides.

Synthesis gas is normally produced by steam reforming a desulphurised hydrocarbon feedstock, especially natural gas. In this process a mixture of steam and a hydrocarbon feedstock is passed, at an elevated temperature and pressure, through externally heated tubes containing a suitable steam reforming catalyst. Catalysts employed are typically nickel on a suitable support, e.g. alumina, magnesia, zirconia, or calcium aluminate cement. The tubes are heated by a suitable gas, typically the product of combusting a suitable fuel. Typically the temperature is in the range 700 to 950° C. and the pressure is in the range 15 to 40, particularly 20 to 30, bar abs. The steam is normally present in an excess over that required for the reforming reaction: in order to reduce the risk of formation of carbon deposits on the reforming catalyst, the steam ratio is typically in the range 1.5 to 4, especially 2 to 3.5. By the term steam ratio is meant the number of gram moles of steam per gram atom of hydrocarbon carbon in the feedstock. The reformed gas will contain hydrogen, carbon monoxide, carbon dioxide, unreacted steam and methane: the precise composition will depend on a variety of factors including the pressure, temperature, and composition of the hydrocarbon/steam mixture. Normally the reformed gas is cooled, with heat recovery, to below the dew point of the steam therein to condense the unreacted steam which is then separated, leaving the residual reformed gas as the synthesis gas.

The Fischer-Tropsch process is often operated by passing the synthesis gas at an elevated temperature and pressure, for example 30 to 50, particularly 35 to 45, bar abs. through a reactor wherein it is contacted with a catalyst, usually an iron- or cobalt-containing composition: a mixture of hydrocarbons is formed together with water and the water and higher hydrocarbons are separated from the residual gas. Conventionally, part of the residual gas is recycled to the reactor as part of the synthesis gas feed, while the remainder of the residual gas is taken as a purge. For the production of hydrocarbons, a stoichiometric synthesis gas has a hydrogen to carbon monoxide molar ratio of about 2, but in order to achieve a high conversion of carbon monoxide, the reactor is often operated with a carbon monoxide-rich gas, i.e. having a hydrogen to carbon monoxide molar ratio below 2, for example having a hydrogen to carbon monoxide molar ratio in the range 1.4 to 1.8, especially 1.4 to 1.6.

Carbon dioxide is largely inert in the Fischer-Tropsch reaction, although some Fischer-Tropsch catalysts exert some activity for the shift and reverse shift reactions:

$$CO + H_2O \rightleftharpoons CO_2 + H_2$$

As a result of the presence of carbon dioxide in the synthesis gas fed to the Fischer-Tropsch reaction and possibly the production of carbon dioxide by the shift reaction by the Fischer-Tropsch catalyst, the purge gas from the Fischer-Tropsch stage contains carbon dioxide as well as some hydrogen and carbon monoxide.

Methanol is normally synthesised from a synthesis gas containing hydrogen and carbon oxides by passing the synthesis gas over a suitable catalyst at an elevated temperature and pressure. The synthesis gas is normally produced by steam reforming as described above. Normally a copper-containing catalyst is employed: suitable catalysts include compositions containing copper, zinc oxide, chromia and/or alumina and possibly other oxidic materials such as magnesia. The reaction is typically operated at temperatures above 200° C. and at pressures in the range 50 to 150, especially 70 to 120, bar abs. The methanol synthesis is generally effected in a loop wherein the synthesis gas as "make-up" gas is mixed with recycled gas, and the mixture fed to the synthesis reactor. The reacted gas from the synthesis reactor is cooled to condense methanol which is then separated and then the residual gas recycled as the recycle gas. To avoid a build-up of inerts, some of the residual gas is taken as a purge. In the methanol synthesis reaction, methanol is synthesised from both carbon monoxide and carbon dioxide. A gas that is stoichiometric for methanol synthesis has a "R" value of 2 where $$R = ([H_2] - [CO_2])/([CO] + [CO2])$$

where $[H_2]$, $[CO_2]$ and $[CO]$ respectively are the molar proportions of hydrogen, carbon dioxide and carbon monoxide.

I have realised that the residual gas from the Fischer-Tropsch reaction may be used as some or all of the feed to a methanol synthesis process: in this way, use may be made of the carbon dioxide, as well as hydrogen and carbon monoxide, in the residual gas from the Fischer-Tropsch process.

Accordingly the present invention provides a process for the co-production of methanol and higher hydrocarbons by synthesising the hydrocarbons from a synthesis gas containing hydrogen, carbon monoxide and carbon dioxide by the Fischer-Tropsch reaction, separating the higher hydrocarbons, and synthesising methanol from the residual gas.

Thus in the present invention, the residual gas from the Fischer-Tropsch stage is used for the synthesis of methanol. As a result the Fischer-Tropsch reaction may be operated on a "once-through" basis, rather than employing a recycle of part of the residual gas remaining after separation of higher hydrocarbon products from the reacted gas from the Fischer-Tropsch reaction.

The synthesis gas resulting from steam reforming of a hydrocarbon feedstock such as natural gas, as described above, will generally have a hydrogen to carbon monoxide ratio of at least 3, and often in the range 4 to 6. Also it generally has a "R" value above 2.5. In order to render the synthesis gas more suited to the Fischer-Tropsch reaction, some of the hydrogen may be separated, for example by a membrane system, in one or more stages, to give a synthesis gas having a hydrogen to carbon monoxide ratio below 2.5, and preferably below 2, e.g. in the range 1.4 to 1.8. When using a membrane separation system, a small amount of the carbon dioxide may also permeate through the membrane with hydrogen. Some or all of the separated hydrogen may be used as fuel, e.g. that combusted to heat the reformer tubes.

The process of the invention may also be employed where steps are taken to produce a reformed gas having a "R" value closer to 2. Thus processes are known for the production of methanol synthesis gas wherein the reformed gas is subjected to a stage of partial combustion with oxygen. This has the effect of removing some of the excess of hydrogen by forming water and hence decreasing the value of "R". Since the partial combustion raises the temperature of the gas it is also possible to decrease the residual methane content of the synthesis gas and hence the amount of inerts fed to the synthesis step. In some known processes, the hot partially combusted gas is used as the heating medium for the reformer tubes.

Whether or not hydrogen is separated to adjust the hydrogen to carbon monoxide ratio to render the synthesis gas more amenable to the Fischer-Tropsch reaction, it will normally be necessary to compress the synthesis gas somewhat from the pressure at which the reforming was effected. Thus while the reforming is preferably effected at a pressure in the range 20 to 30 bar abs., the Fischer-Tropsch reaction is preferably effected at a pressure in the range 35 to 45 bar abs.

In a preferred process the synthesis gas is produced by reforming and separation of the excess of steam as described above and then passed through a membrane separation unit to remove some hydrogen, and then at least some of the non-permeate from the membrane separation unit is compressed and at least some of the compressed gas is passed through a second membrane separation unit to separate a further amount of hydrogen. Some of the non-permeate from the first membrane separation unit may bypass the second membrane separation unit: the pressure energy in the non-permeate from the second membrane separation unit may be used to compress the gas which has bypassed the second membrane separation unit.

The non-permeate from the second membrane unit, preferably with any bypass thereof, is used as the feed to the Fischer-Tropsch reactor and the off-gas, i.e. residual gas after separation of the higher hydrocarbons, from the Fischer-Tropsch reaction is used to make methanol, e.g. by use as make-up gas for a methanol synthesis loop, preferably after further compression. Where hydrogen is separated from the reformed gas prior to the Fischer-Tropsch synthesis, it is generally desirable to re-introduce some or all of this hydrogen into the Fischer-Tropsch off-gas prior to methanol synthesis. Where the hydrogen is separated by means of two membrane separation units with compression between the two separation stages as described above, it is preferred that the hydrogen added to the off-gas prior to methanol synthesis, is at least part of the hydrogen separated in the second separation stage.

The Fischer-Tropsch reaction is well known and may be operated using any of the usual technologies and reactor designs. Preferably the Fischer-Tropsch reactor is of the slurry reactor type. The Fischer-Tropsch reaction is exothermic and heat is usually recovered from the reaction, e.g. by the provision of suitable cooling coils. The recovered heat may be used to raise steam. Unlike conventional Fischer-Tropsch reactions, however, as described above, in the present invention it is preferred not to recycle part of the off-gas to the Fischer-Tropsch synthesis. In the Fischer-Tropsch reactor some of the carbon monoxide and hydrogen combine to form hydrocarbon compounds together with by-product water. Preferably the Fischer-Tropsch reaction is effected under such conditions that about 50% to 80%, especially 50% to 65%, of the carbon monoxide in the feed to the Fischer-Tropsch reactor is reacted to hydrocarbons. The products of the Fischer-Tropsch reaction range from methane through liquid hydrocarbons to waxes. The condensed products may mainly comprise $C_4$ to $C_{20}$ compounds. The hydrocarbons are largely straight chained paraffins. The higher hydrocarbon product is separated from the Fischer-Tropsch catalyst and the residual gas is extracted from the Fischer-Tropsch reactor by means known in the art. The residual gas may be cooled to separate and recover some of the more volatile hydrocarbon products and the water formed during the Fischer-Tropsch reaction. Methane, and other lower hydrocarbons, are generally not separated from the gas stream but can be used as fuel and/or at least part recycled as described hereinafter and/or used as part of The reformer feed. The higher hydrocarbon products may be separated by distillation into a LPG fraction, naphtha, diesel and wax. Often the higher molecular weight components, e.g. waxes, may be subjected to mild hydro-cracking and isomerisation processes. For hydro-cracking, hydrogen is required. This may be supplied from hydrogen separated from the reformed gas prior to the Fischer-Tropsch reaction and/or from hydrogen separated from the purge gas from the methanol synthesis stage. The main cracked product resulting from hydro-cracking of the wax fraction is diesel, which is preferably returned to a suitable place in the Fischer-Tropsch products separation section. Using this process, a sulphur-free uncracked diesel of cetane number of about 80, together with a cracked diesel of cetane number of about 65 can be produced. Preferably the LPG fraction is recycled back to the Fischer-Tropsch reactor. The naphtha fraction has a very straight chain and is particularly suitable for ethylene production.

The off-gas from the Fischer-Tropsch reaction is then used for methanol synthesis. Normally it will be sent to the make-up gas compressor of the methanol synthesis stage and from there into a methanol synthesis loop.

The methanol synthesis stage is normal although the gas composition may be richer in inerts (methane) and carbon dioxide than is normally encountered in methanol synthesis. In spite of the relatively higher carbon dioxide content of the synthesis gas fed to the methanol synthesis loop, efficient methanol synthesis may be achieved since the synthesis gas may have a composition closer to stoichiometric for methanol synthesis than in a normal methanol synthesis loop. The increased carbon dioxide content will also result in the production of a greater amount of water than is normal in methanol synthesis and hence increase the distillation duty. However, heat recovered from the Fischer-Tropsch reaction may be used to supply energy required for such distillation. As a result of the present invention, it is likely that traces of higher hydrocarbons will be present in the off-gas fed to the methanol synthesis stage and hence may appear in the product methanol, and be detectable even after the usual distillative purification stages. To avoid a large inerts content in the methanol synthesis loop, a larger purge than normal may be required. Hydrogen may be recovered from the purge for use in a hydro-cracker as indicated above. Part of the purge may be recycled as part of the hydrocarbon feedstock to the reformer: In this way part of the carbon "lost" by formation of lower hydrocarbons such as methane in the Fischer-Tropsch process can be recovered.

The process of the invention may be applied to an existing methanol or Fischer-Tropsch plant. Thus if there is no economic market for part of the output of an existing methanol plant, for example as a result of global or local over-capacity, it may be more economic to convert the plant to operate the present invention rather than to run the unmodified plant at a reduced throughput. Where there are two adjacent methanol plants, by adoption of the present invention, the reforming stages of both plants may be used, but the synthesis loop of one plant closed down. Thus in the event that about half of the carbon in the original synthesis gas produced from the reforming stages of the adjacent plants is converted to Fischer-Tropsch products then the off-gas from the Fischer-Tropsch stage can be compressed to the desired methanol synthesis pressure using the synthesis gas compressor of only one of the adjacent plants and fed to the synthesis loop of that plant. Despite the increased carbon dioxide content of the synthesis gas fed to the loop, it should still be possible to maintain the output from the one operating synthesis loop at close to its original output partly because the loop would then be running at closer to its stoichiometric ratio. Where, as described above, prior to feeding to the Fischer-Tropsch synthesis, some or all of the reformed gas, possibly after separation of some of the hydrogen, is compressed, the compression may be effected in the synthesis gas compressor of the other of the adjacent methanol plants. This method of integrating the Fischer-Tropsch process with two methanol plants has the advantage of allowing the Fischer-Tropsch plant to be built and then only requiring a very short shutdown of the methanol plants to tie in the Fischer-Tropsch plant to the methanol plants.

In applying the invention to an existing methanol plant or plants, other changes that may result may be the use of separated hydrogen as fuel for the steam reforming stage, and as the hydrogen-containing gas often required to be added prior to desulphurisation of the feedstock.

If this idea is applied to integrating two adjacent 2500 tonnes per day (tpd) methanol plants, then about 1000 to 1100 tpd of hydrocarbons can be produced in the Fischer-Tropsch stage. Steam from the Fischer-Tropsch heat of reaction may be used to replace any methanol synthesis loop heat lost because of the lower methanol production rate and because the methanol will now be produced more from carbon dioxide than from carbon monoxide, e.g. to provide energy for a natural gas saturator in one of the synthesis gas generation units, or to provide some or all of the heat needed to separate the Fischer-Tropsch products, preferably by distillation. About 1000 to 1100 tpd of water is also produced by the Fischer-Tropsch reaction and may be used to reduce the need to import water for the plant. In round terms this would halve the water make-up requirements. Where the steam required for reforming is introduced into the hydrocarbon feedstock by saturation, i.e. where the feedstock is contacted with a stream of heated water under pressure, the water produced by the Fischer-Tropsch reaction could be used as part of the water used for saturation: This would serve to recycle any dissolved or entrained hydrocarbons.

BRIEF DESCRIPTION OF THE DRAWING

The invention is further illustrated by reference to the drawing.

Figure 1:
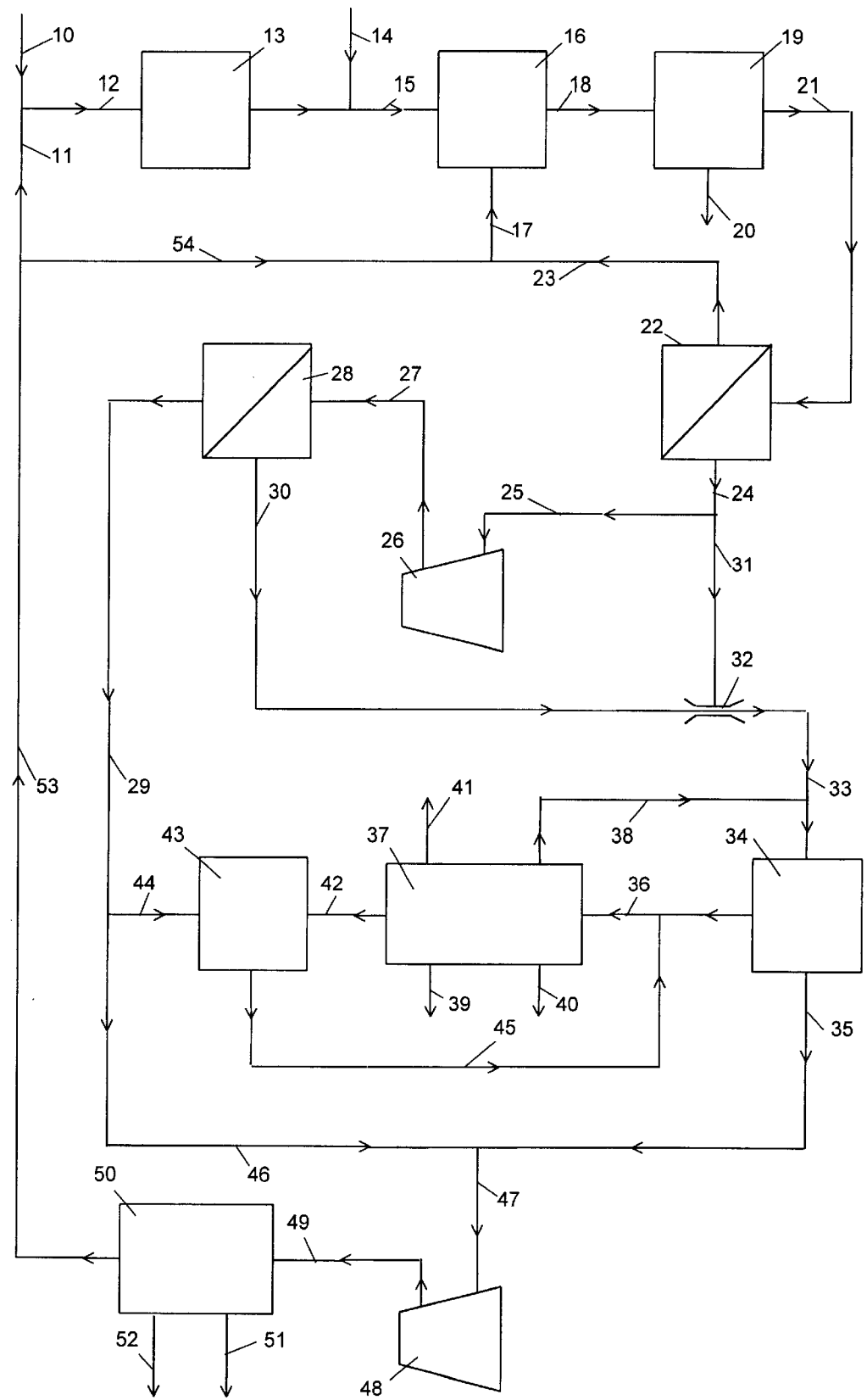
FIG. 1 is a diagrammatic flow sheet of a plant in accordance with the invention.

Referring to the drawing, a feedstock, such as natural gas, at an elevated pressure, typically about 20 bar abs., is supplied via line 10, mixed with a hydrogen-containing gas stream 11 and fed via line 12 to a desulphurisation stage 13 including hydro-desulphurisation to convert organic sulphur compounds to hydrogen sulphide followed by absorption of hydrogen sulphide. Steam supplied via line 14 is mixed with the desulphurised feedstock and fed via line 15 to a reforming stage 16. The steam may be supplied as such and/or by saturating the desulphurised feedstock by contact thereof with heated water.

In the reforming stage 16, the feedstock/steam mixture is heated and passed over a steam reforming catalyst disposed in tubes heated by combustion of a fuel supplied via line 17. The resultant reformed gas, containing hydrogen, carbon oxides, methane and steam, together with any inerts such as nitrogen that were present in the feedstock, is then fed via line 18 to a cooling/water separation stage 19. Condensed water is separated via line 20 and may be used to form part of the steam supplied via line 14.

The de-watered reformed gas is then fed via line 21 to a first membrane separation unit 22. Some of the hydrogen, and a small amount of the carbon dioxide present in the de-watered reformed gas, permeate the membrane and form a permeate stream 23 which is used as part of the fuel stream 17 combusted in the reforming stage, leaving an impermeate stream 24. Part, for example 50 to 60% by volume, of the impermeate stream 24 is fed via line 25 to a first compressor 26 wherein it is compressed to for example about 35 bar abs., and then fed via line 27 to a second membrane separation unit 28. This is operated with the permeate stream at an elevated pressure, for example 20 bar abs. A further amount of hydrogen permeates the membrane and forms the permeate stream 29, while the impermeate stream 30 from the second membrane unit 28 is mixed with the remainder 31 of the impermeate stream 24 from the first membrane unit 22. The stream 31 may be added to the stream 30 by using the latter as the driving gas for an ejector 32 into which stream 31 is drawn.

The mixture of streams 30 and 31 is fed via line 33 to a Fischer-Tropsch synthesis unit 34. The amount of hydrogen separated in the membrane separation units is such that the feed to the Fischer-Tropsch synthesis unit 34 has the desired hydrogen to carbon monoxide molar ratio, preferably below 2 and particularly in the range 1.4 to 1.8.

In the Fischer-Tropsch synthesis unit, which is typically of the bubble slurry type employing a cobalt catalyst, hydrogen and carbon monoxide in the gas fed via line 33 reacts to form hydrocarbons and water. Cobalt catalysts have the advantage that only a small proportion of the carbon monoxide present is converted to carbon dioxide by the shift reaction. The Fischer-Tropsch reactor is preferably operated under such conditions that about 50 to 80% of the carbon monoxide in the feed line 33 is converted into hydrocarbons. The residual gaseous phase is discharged from the Fischer- Tropsch reactor via line 35, while the liquid phase is fed via line 36 to a separation unit 37 wherein the liquid phase is separated into fractions, e.g. by distillation. The lowest boiling fraction is recycled via line 38 to the Fischer-Tropsch feed line 33. Liquid higher hydrocarbons, e.g. naphtha and diesel fractions, are separated as one or more streams 39, 40, and water separated as a stream 41. This water may be recycled to form part of the feed used to produce the steam 14 required for steam reforming. Also separated from the separation unit 37 is a high boiling hydrocarbon wax fraction. This is fed via line 42 to a hydro-cracking unit 43 where it is reacted with a part stream 44 of the hydrogen permeate stream 29 from the second membrane separation unit 28. The hydro-cracking unit 43 is operated under relatively mild conditions so that it converts the waxes to lower boiling hydrocarbons, primarily corresponding to the diesel fraction. The hydro-cracking unit product is then fed, via line 45, back to the feed 36 to the separation unit 37.

The residual gas stream 35 from the Fischer-Tropsch reactor is mixed with the remainder 46 of the permeate stream 29 from the second membrane separation unit and fed, via line 47 to a synthesis gas compressor 48. Preferably the amount of the remainder 46 of the permeate 29 and the conditions of the Fischer-Tropsch reaction 34 is such that the mixture of streams 35 and 46 has a "R" value in the range 2.0 to 2.2. The mixture is compressed in compressor 48 to a pressure suitable for methanol synthesis, typically in the range 60 to 120 bar abs., e.g. about 90 bar abs. The compressed synthesis gas is then fed via line 49 to a methanol synthesis stage 50 wherein methanol is synthesised, separated and purified, normally by distillation. The methanol synthesis stage may include a loop as described above. The purified methanol is discharged via line 51, the water separated during the distillation is discharged via line 52 and may be used to form part of the steam supplied to the reformer via line 14. A purge stream 53 is discharged from the methanol synthesis stage 50 to avoid a build-up of inerts in the synthesis stage. Part of the purge stream 53 is used as the hydrogen-containing gas supplied to the hydrocarbon feedstock via line 11 while the remainder is fed via line 54 to form the remainder of the fuel fed via line 17 to the reformer 16.

Alternatively, all of the purge stream 53 is fed via line 54 and used as fuel for the reformer and/or other purposes and the hydrogen-containing stream 11 provided by part of the permeate stream 23.

Where two adjacent methanol plants are modified in accordance with the invention, it will be appreciated that the desulphurisation, reforming and de-watering stages 13, 16, 19 will be duplicated and operated in parallel with the output then being combined and fed to the membrane unit 22. Alternatively the de-watered reformed gas from one reformer train may be fed to the membrane separation unit and that from the other reformer train fed directly as part of the Fischer-Tropsch feed 33, e.g. as part of the bypass stream 31. The compressor 26 may be one or more stages of the synthesis gas compressor of one methanol plant; the compressor 48 is the synthesis gas compressor of the other methanol plant. The methanol synthesis stage of one of the two plants is not used.

As a calculated example of a process in accordance with the above flowsheet, flow rates of the components are given in the following table, scaled to 10000 kmol/h of the de-watered reformed gas.

|  | Flow rate (kmol/h) | | | | | | | | |
| --- | --- | --- | --- | --- | --- | --- | --- | --- | --- |
|  | $CH_4$ | $CO_2$ | CO | $N_2$ | $H_2$ | $CH_3OH$ | $H_2O$ | $C_4H_{10}$ | $C_{12}H_{26}$ |
| Stream 21 | 310 | 784 | 1609 | 27 | 7271 | | | | |
| Stream 33 | 305 | 689 | 1586 | 27 | 3410 | | | | |
| Streams 39–41 | 60 | | | | | | 1204 | 10 | 92 |
| Stream 47 | 366 | 716 | 389 | 27 | 3540 | | | | |
| Stream 51 | | | | | | 988 | | | |

The components $C_4H_{10}$ and $C_{12}H_{26}$ are used to represent products for mass balance only. The actual products will be a range of hydrocarbons. Thus about 760 tpd of methanol and about 390 tpd of higher hydrocarbons are produced per 10000 kmol/h of dewatered reformed gas.

What is claimed is:

1. A process for the co-production of methanol and higher hydrocarbons by synthesising the hydrocarbons from a synthesis gas containing hydrogen, carbon monoxide and carbon dioxide by the Fischer-Tropsch reaction, separating the higher hydrocarbons, and synthesising methanol from the residual gas.

2. A process according to claim 1 wherein the synthesis gas is produced by steam reforming a hydrocarbon feedstock followed by separation of the excess of steam therein to give a de-watered reformed gas and part of the hydrogen in the de-watered reformed gas is separated from the de-watered reformed gas to give the synthesis gas fed to the Fischer-Tropsch reaction.

3. A process according to claim 2 wherein part of the separated hydrogen is added to the residual gas after the Fischer-Tropsch reaction but before the methanol synthesis.

4. A process according to claim 2 wherein the hydrogen is separated in at least one membrane separation stage.

5. A process according to claim 4 wherein at least part of the non-permeate from a first membrane separation stage is compressed and fed to a second membrane separation stage to separate a further amount of hydrogen and the non-permeate from the second membrane separation stage, together with at least some of the remainder, if any, of the non-permeate from the first membrane separation stage, is fed as the synthesis gas to the Fischer-Tropsch reaction and the permeate from the second membrane separation stage is added to the residual gas after Fischer-Tropsch reaction but before methanol synthesis.

6. A process according to claim 3 wherein the de-watered reformed gas has a hydrogen to carbon monoxide molar ratio of at least 3 and the amount of hydrogen separated from the de-watered reformed gas is such that the synthesis gas fed to the Fischer-Tropsch reaction has a hydrogen to carbon monoxide molar ratio below 2.5, and the amount of separated hydrogen added to the residual gas prior to methanol synthesis is such that the resultant mixture of hydrogen and residual gas has a "R" value in the range 2.0 to 2.2 where $R=([H_2]-[CO_2])/([CO]+[CO2])$ where $[H_2]$, $[CO_2]$ respectively are the molar proportions of hydrogen, carbon dioxide and carbon monoxide in the mixture.

7. A process according to claim 2 wherein the higher hydrocarbon products from the Fischer-Tropsch reaction are separated into fractions, including a wax fraction, in a product separation unit and the wax fraction is fed to a hydro-cracking unit wherein the wax fraction is hydro-cracked using some of the separated hydrogen and the hydro-cracked wax product is returned to the product separation stage.

8. A method of modifying a methanol plant for the co-production of methanol and higher hydrocarbons wherein the methanol plant includes a synthesis gas generation stage including steam reforming a hydrocarbon feedstock and subsequent removal of excess steam to give a de-watered reformed gas as the synthesis gas, one or more stages of compression of the synthesis gas and a stage of methanol production from the resultant compressed synthesis gas, comprising introducing a Fischer-Tropsch stage between said synthesis gas generation stage and the methanol production stage, said Fischer-Tropsch stage including a stage of Fischer-Tropsch synthesis wherein a synthesis gas is reacted to produce higher hydrocarbons leaving a residual gas and a stage of separation of higher hydrocarbons from the residual gas, whereby the residual gas from the Fischer-Tropsch stage is compressed in one or more of said compression stages and fed to the methanol production stage.

* * * * *